(12) United States Patent
Kuo et al.

(10) Patent No.: US 9,964,477 B2
(45) Date of Patent: May 8, 2018

(54) METHOD OF DETECTING PRELOAD OF LINEAR GUIDE

(71) Applicant: HIWIN TECHNOLOGIES CORP., Taichung (TW)

(72) Inventors: Chang-Hsin Kuo, Taichung (TW); Po-Lin Lee, Taichung (TW)

(73) Assignee: Hiwin Technologies Corp., Taichung (TW)

( * ) Notice: Subject to any disclaimer, the term of this patent is extended or adjusted under 35 U.S.C. 154(b) by 118 days.

(21) Appl. No.: 15/094,331

(22) Filed: Apr. 8, 2016

(65) Prior Publication Data

US 2017/0292900 A1  Oct. 12, 2017

(51) Int. Cl.
*G01N 3/30* (2006.01)
*G01M 7/02* (2006.01)
*G01P 15/09* (2006.01)

(52) U.S. Cl.
CPC ............ *G01N 3/30* (2013.01); *G01M 7/02* (2013.01); *G01P 15/09* (2013.01)

(58) Field of Classification Search
CPC ............ G01N 3/30; G01P 15/09; G01M 7/02
See application file for complete search history.

(56) References Cited

U.S. PATENT DOCUMENTS 7,503,216 B2 * 3/2009 Yamada .................. F16C 19/52
                                                          73/593

OTHER PUBLICATIONS

Hung et al. ("Fault Detection of Linear Guide Preload of a Positioning Stage with Vibration—Acoustic Analysis", ASM International 2011, see attached publication).*
Schwarz et al. ("Experimental Modal Analysis", Vibrant Technology, Inc. 1999, see attached publication).*

* cited by examiner

*Primary Examiner* — Paul West
*Assistant Examiner* — Xin Zhong
(74) *Attorney, Agent, or Firm* — Muncy, Geissler, Olds & Lowe, P.C.

(57) ABSTRACT

A method of detecting a preload of a linear guide includes: applying an external force to the linear guide with an external force applying device, wherein the external force applying device sends an impact signal while applying the external force; sensing with a sensor a vibration signal sent from the linear guide because of vibration thereof which occurs under the external force; and receiving the impact signal of the external force applying device and the vibration signal of the sensor and calculating the preload of the linear guide according to a received result, with a signal analyzer. Therefore, with the method of the present invention, the preload of the linear guide is precisely tested regardless of environmental factors.

7 Claims, 8 Drawing Sheets

METHOD OF DETECTING PRELOAD OF LINEAR GUIDE

BACKGROUND OF THE INVENTION

1. Technical Field

The present invention relates to linear guides and more particularly to a method of detecting a preload of a linear guide.

2. Description of Related Art

A linear guide comprises rolling elements, such as balls or rollers, a carriage, and a rail. The rolling elements circulate within the carriage to enable the carriage move along the rail undergo high-precision. However, due to the friction and collision between the rail and rolling elements, the linear guide is likely to vibrate in the course of high-speed motion, thereby ending up with a shortened service life. In an attempt to overcome the aforesaid drawback of the prior art, it is advisable to apply a preload to the linear guide with a view to enhancing structural rigidity and eliminating gaps.

Regarding a preload applied to a linear guide, the conventional test method entails calculating the friction between the rail and rolling elements according to the thrust required for the carriage and then calculating the range of the preload according to the linear relationship between the friction and the preload. However, the aforesaid test method has a drawback as follows: the friction is subject to errors arising from the environments of the linear guide, and in consequence the preload thus calculated is imprecise.

SUMMARY OF THE INVENTION

It is an objective of the present invention to provide a method of detecting a preload of a linear guide with high precision.

In order to achieve the above and other objectives, the present invention provides a method of detecting a preload. The method of detecting a preload takes several steps. The first step involves applying an external force to a linear guide with an external force applying device, wherein the external force applying device sends an impact signal while applying the external force. The second step involves sensing with a sensor a physical quantity signal sent from the linear guide because of the vibration thereof the external force, wherein the physical quantity signal relates to displacement, velocity, acceleration or pressure. The third step involves receiving the impact signal of the external force applying device and the physical quantity signal of the sensor with a signal analyzer, and calculating a preload of the linear guide according to a received result.

Therefore, the test method of the present invention dispenses with the hassles of calculating the friction and thus precludes the negative effects of environmental factors on the test result, thereby enhancing the test precision.

DETAILED DESCRIPTION OF THE EMBODIMENT OF THE INVENTION

Figure 1:
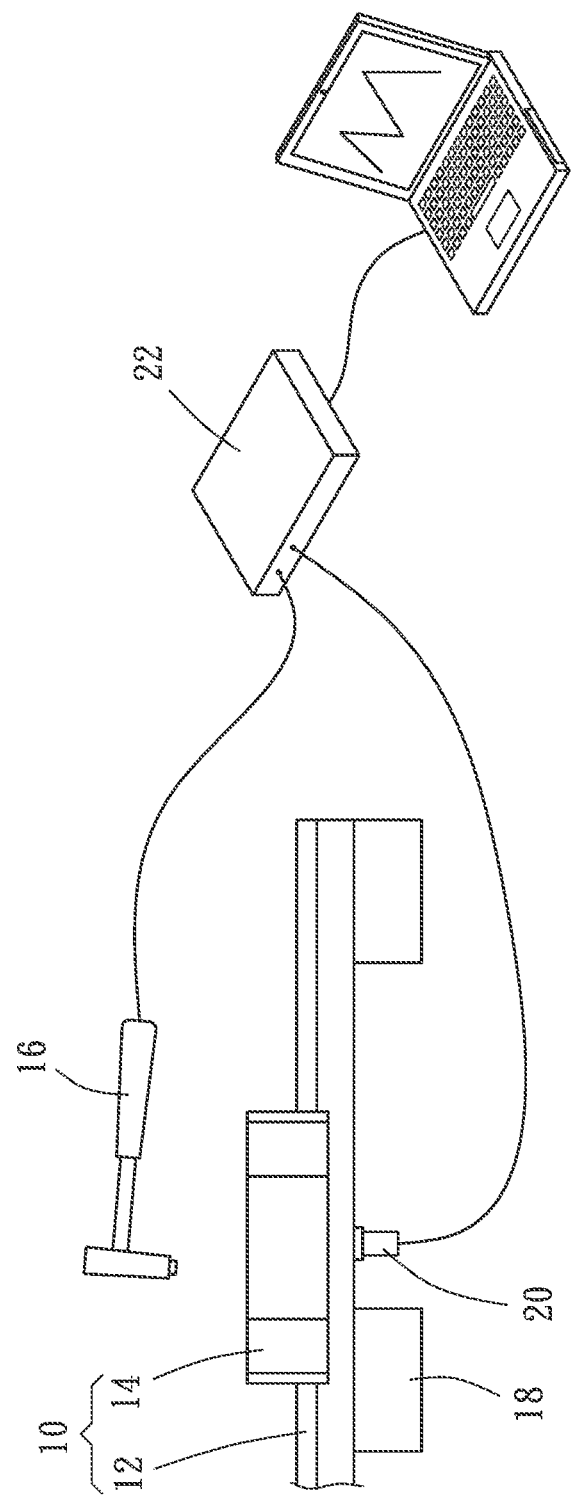
FIG. 1 is a structural schematic view of a method of detecting a preload according to an embodiment of the present invention.
Figure 3:
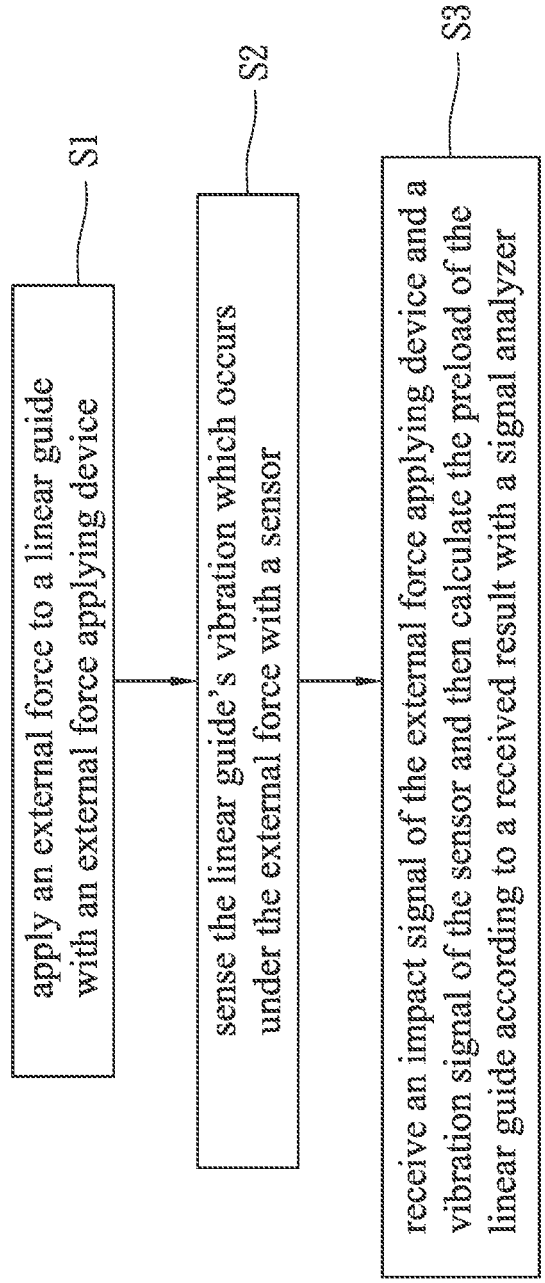
FIG. 3 is a schematic view of the process flow of the method of detecting a preload according to the embodiment of the present invention.

Referring to FIG. 1, a linear guide 10 comprises a rail 12 and a carriage 14 slidably disposed at the rail 12. Referring to FIG. 3, according to the present invention, a method of detecting a preload comprises the steps described below.

Step a) S1: applying an external force to the carriage 14 of the linear guide 10 with an external force applying device 16 operated with a robotic arm or by hand, wherein the external force applying device 16 sends an impact signal while applying the external force. The external force applying device 16 is an impact hammer or an vibration shaker, but the present invention is not limited thereto. Before starting to operate the external force applying device 16, it is feasible to mount the linear guide 10 on a base 18 to thereby prevent the linear guide 10 from undergoing any displacement under the external force exerted by the external force applying device 16. The base 18 has less rigidity than the linear guide 10, as in an embodiment of the present invention where the base 18 is made of sponge, to preclude erroneous measurement in the course of the test. Alternatively, the base 18 has larger rigidity than the linear guide 10, as in a variant embodiment of the present invention where the base 18 is made of conventional flooring. The present invention is not restrictive of the material which the base 18 is made of.

Step b) S2: sensing with a sensor 20 a physical quantity signal sent from the linear guide 10 because of the vibration thereof which occurs under the external force. The sensor 20 is an accelerometer, velocity sensor, displacement sensor or microphone, but the present invention is not limited thereto.

Referring to FIG. 1, the sensor 20 is a piezoelectric accelerometer. The sensor 20 is directly attached to the linear guide 10. The physical quantity signal, which is sent from the linear guide 10 because of the vibration thereof which occurs under the external force and received by the sensor 20, relates to acceleration.

Figure 2:
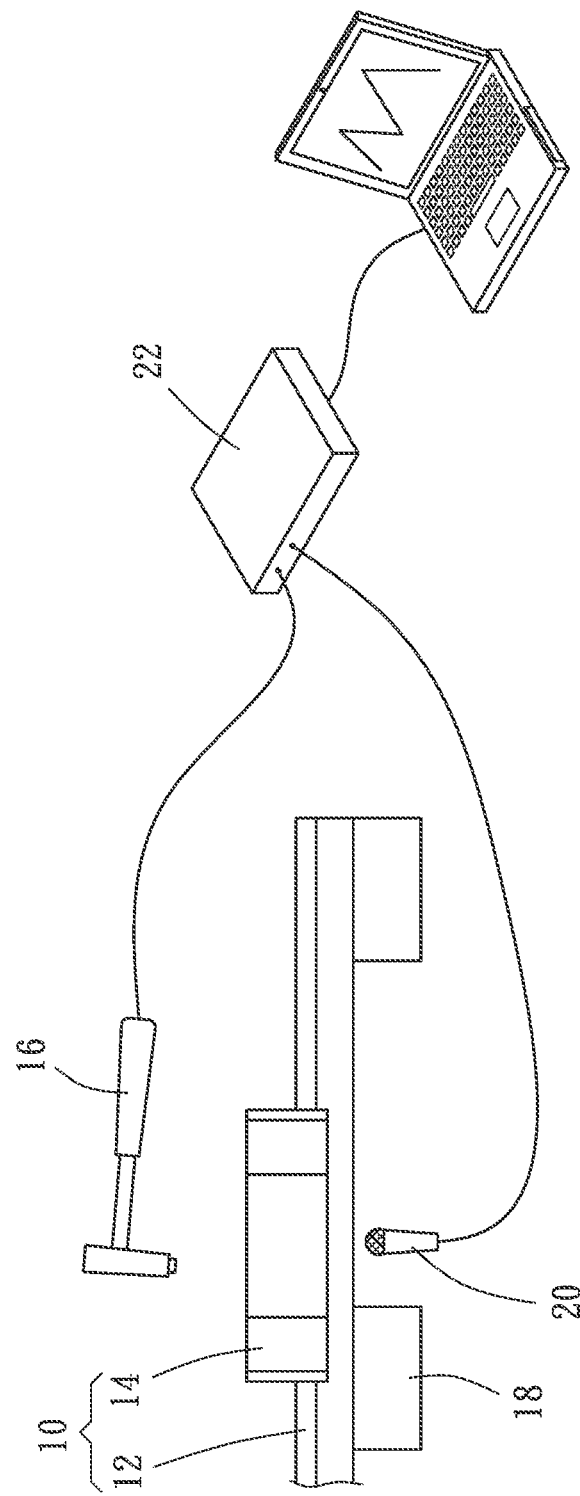
FIG. 2 is another structural schematic view of the method of detecting a preload according to the embodiment of the present invention.

Referring to FIG. 2, the sensor 20 is a microphone for use in measurement. The sensor 20 is separated from the linear guide 10 by a distance and thus is not in contact with the linear guide 10. The physical quantity signal, which is sent from the linear guide 10 because of the vibration thereof which occurs under the external force and received by the sensor 20, relates to sound pressure.

Step c) S3: receiving the impact signal of the external force applying device 16 and a vibration signal of the sensor 20, calculating a frequency response function (FRF) according to the ratio of impact signal to vibration signal, and calculating the preload of the linear guide 10 in accordance with a frequency change shown by the FRF, with a signal analyzer 22. The ratio of impact signal to vibration signal is calculated by using a denominator which is a value obtained as a result of the conversion of the impact signal or vibration signal.

A transfer function is a mathematical relation between an input factor and an output result of a phenomenon when the phenomenon is mathematically described. For instance, given a mathematical relation y=ax, where y denotes output, x denotes input, then y/x=a, where a denotes the mathematical relation between output y and input x, thereby providing a transfer function of a control system.

Figure 4:
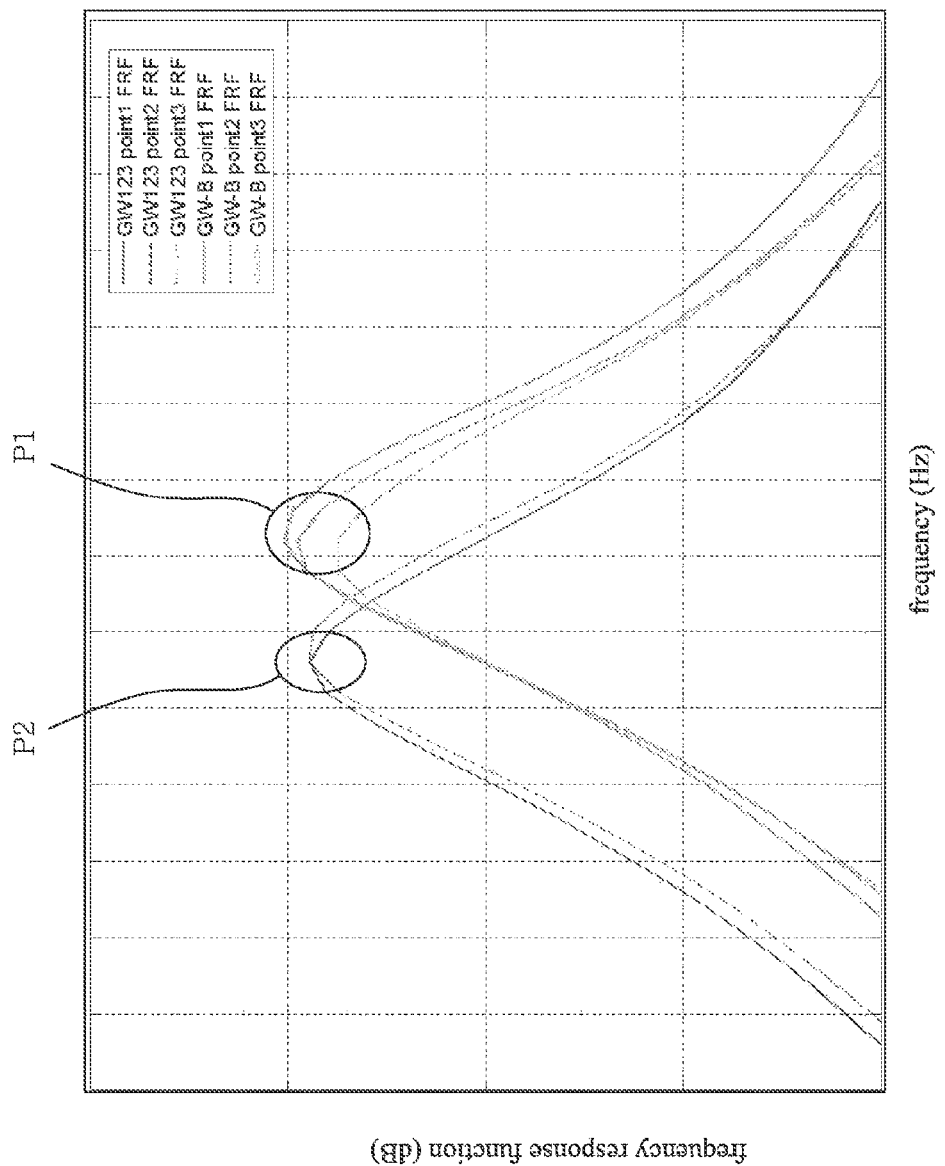
FIG. 4 shows graphs of the results of experiments conducted on three carriages which differ in preload.

Referring to FIG. 4, there are shown graphs of functions illustrative of the results of experiments conducted on three carriages being knocked thrice under different preload values and in the same position, wherein the three carriages each have a first preload value (P1) and a second preload value, wherein the first preload value (P1) is larger than the second preload value (P2). As shown in FIG. 4, carriages with the same preload value behave in the same way at the peak value of a natural frequency.

Figure 5:
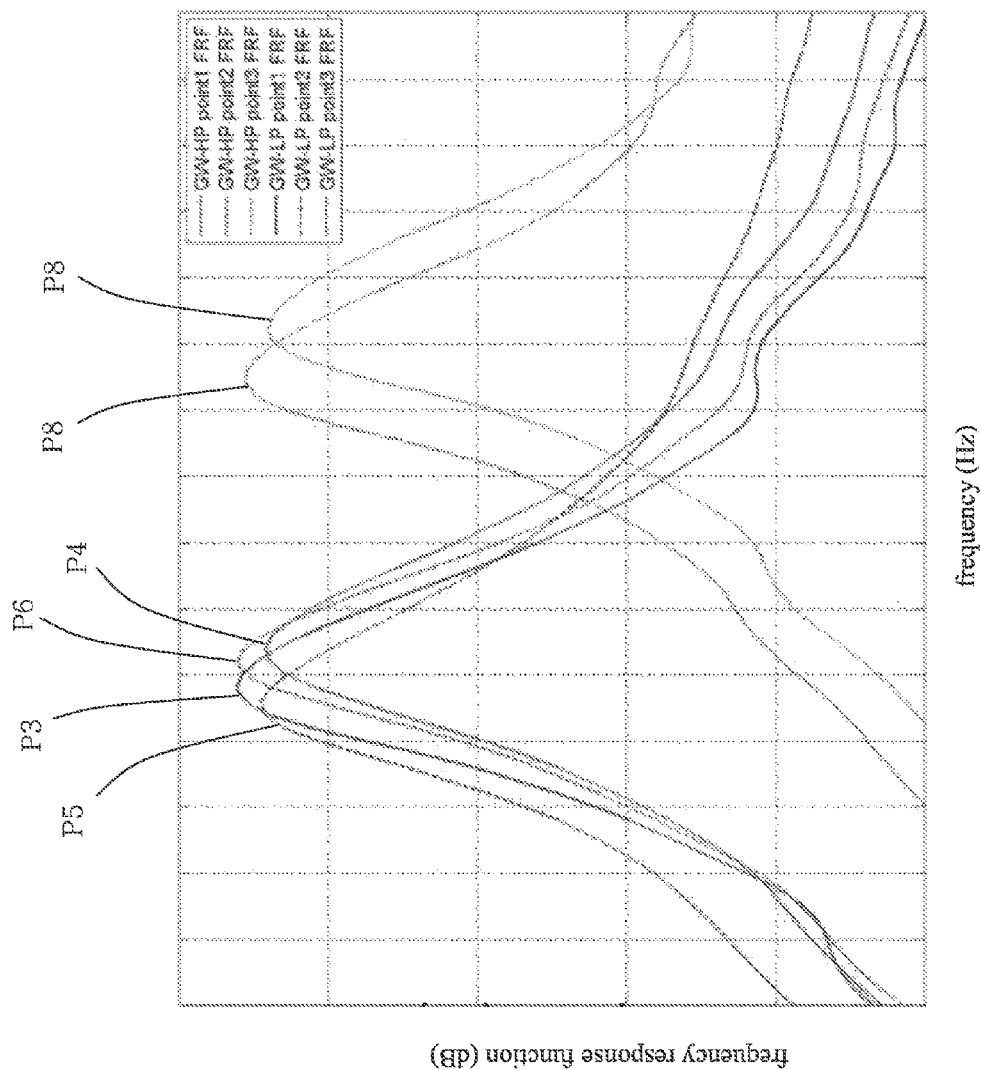
FIG. 5 shows graphs of the results of experiments conducted on the carriages in three different knock directions.
Figure 6A:
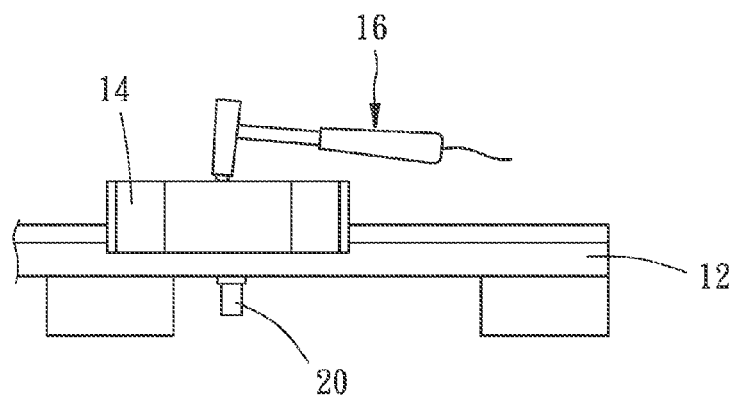
FIGS. 6a~6c are structural schematic views of the method of detecting a preload according to the present invention, showing three different knock directions of the carriages.
Figure 6B:
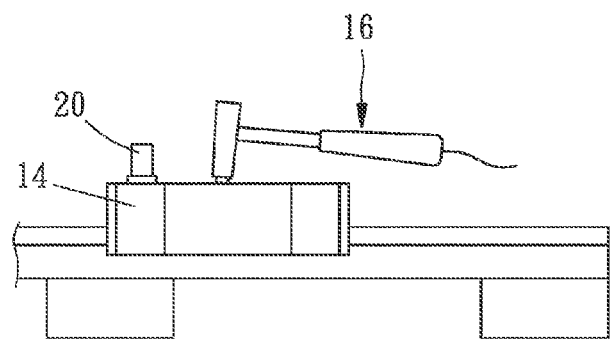
Figure 6C:
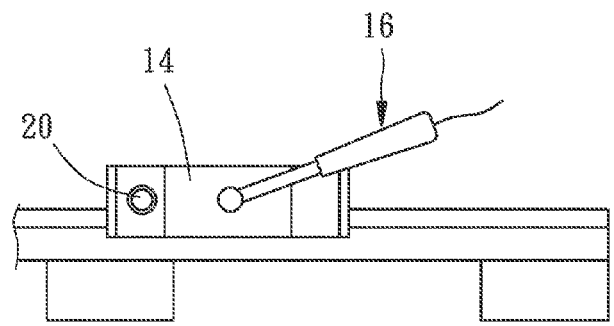

FIG. 5 shows graphs of functions illustrative of the results of experiments conducted on two carriages 14, which differ in preload, sensed in three different knock directions. FIG. 6a shows that the external force applying device 16 knocks the carriage 14 on the top surface thereof and shows that the sensor 20 is mounted on the bottom surface of the rail 12. The result of the experiment illustrated with FIG. 6a is shown in FIG. 5 as follows: P3 denotes the carriage 14 with a small preload value, and P4 denotes the carriage 14 with a large preload value. FIG. 6b shows that the external force applying device 16 knocks the carriage 14 on the top surface thereof and shows that the sensor 20 is mounted on the top surface of the carriage 14. The result of the experiment illustrated with FIG. 6b is shown in FIG. 5 as follows: P5 denotes the carriage 14 with a small preload value, and P6 denotes the carriage 14 with a large preload value. FIG. 6c shows that the external force applying device 16 knocks the carriage 14 on a lateral surface thereof and shows that the sensor 20 is mounted on the knocked lateral surface of the rail 12. The result of the experiment illustrated with FIG. 6c is shown in FIG. 5 as follows: P7 denotes the carriage 14 with a small preload value, and P8 denotes the carriage 14 with a large preload value. Therefore, the knock direction affects the peak value of the natural frequency, but it is still possible to discern the difference in preload between two carriages 14.

Figure 7:
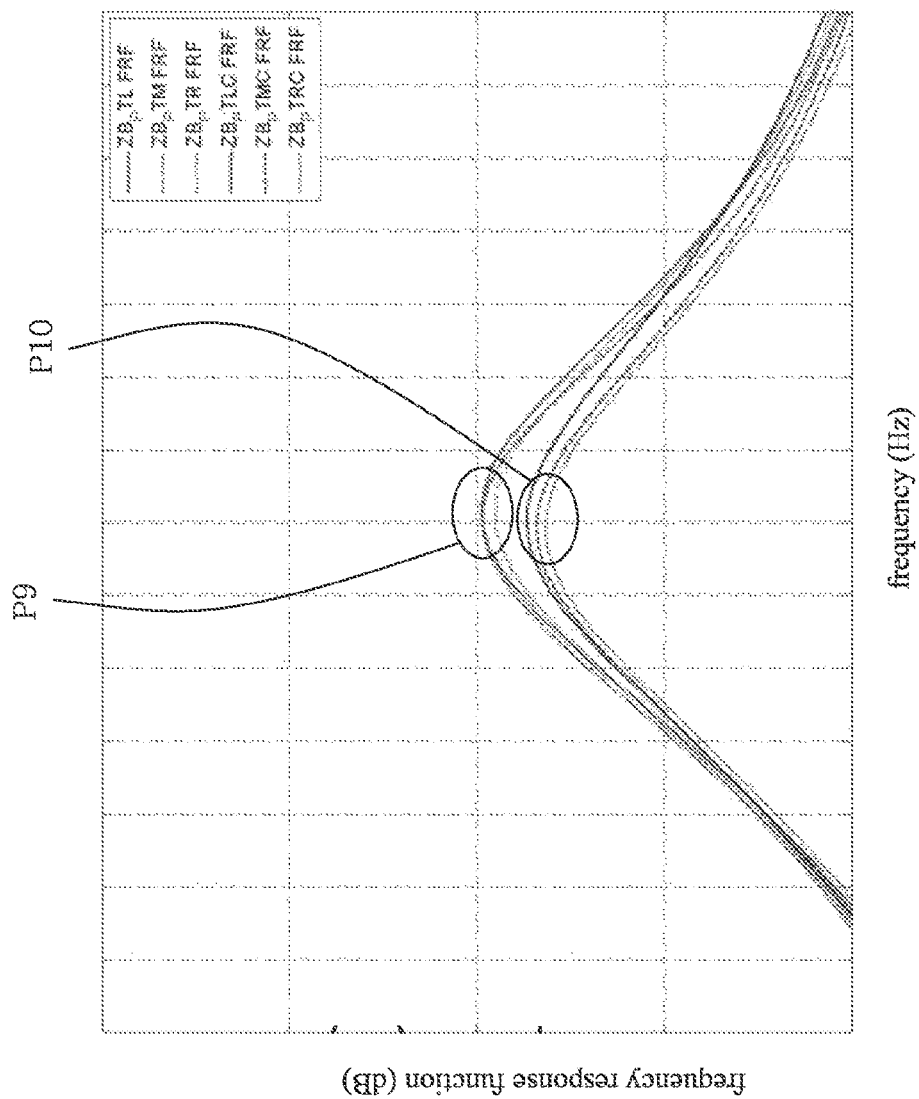
FIG. 7 shows graphs of the results of experiments conducted on the same carriage at three different knock positions and in two scenarios, namely a linear guide flawed with assembly-related errors and a linear guide free of assembly-related errors.
Figure 8A:
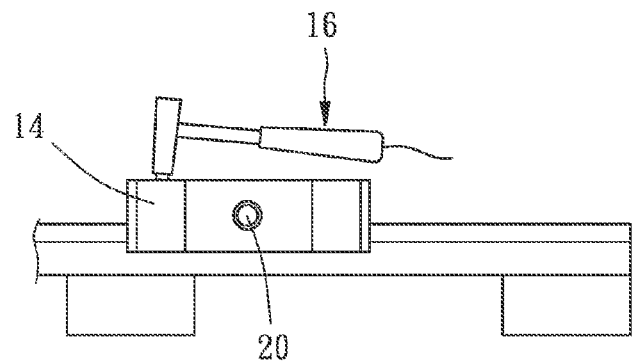
FIGS. 8a~8c are structural schematic views illustrative of three different knock positions of the carriages.
Figure 8B:
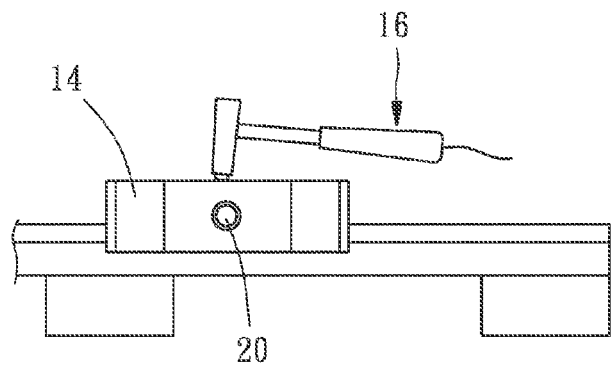
Figure 8C:
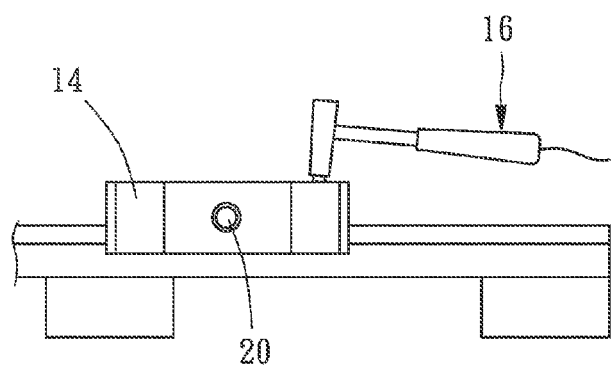

FIG. 7 shows graphs of functions illustrative of the results of experiments conducted on the same carriage at three different knock positions. The knock positions are shown in FIGS. 8a~8c, where the external force applying device 16 knocks at the left position, the central position, and the right position of the top surface of the carriage 14, and the sensor 20 is mounted on a lateral surface of the carriage 14, indicating that the peak value of the natural frequency remains unaffected, despite the different knock positions of the carriage 14. Referring to FIG. 7, the FRF above is attributed to the situation where a linear guide is free of any assembly-related errors and P9 denotes the peak value of the natural frequency, whereas the FRF below is attributed to the situation where a linear guide is flawed with assembly-related errors and P10 denotes the peak value of the natural frequency. As shown in FIG. 7, the peak value of the natural frequency remains unaffected, regardless of whether the same linear guide is flawed with assembly-related errors.

Therefore, the test method of the present invention dispenses with the hassles of calculating the friction and thus precludes the negative effects of environmental factors on the test result, thereby enhancing the test precision.

What is claimed is:

1. A method of detecting a preload of a linear guide, comprising the steps:
    a) applying an external force to the linear guide with an external force applying device, wherein the external force applying device sends an impact signal while applying the external force;
    b) sensing with a sensor a physical quantity signal sent from the linear guide because of vibration thereof which occurs under the external force; and
    c) receiving the impact signal of the external force applying device and the physical quantity signal of the sensor, and calculating the preload of the linear guide according to a received result, with a signal analyzer;
    wherein the signal analyzer calculates a frequency response function according to a ratio of the impact signal of the external force applying device to the physical quantity signal of the sensor and then calculates the preload of the linear guide in accordance with the frequency response function.

2. The method of claim 1, wherein, before operation of the external force applying device starts, the linear guide is mounted on a base to prevent the linear guide from undergoing any displacement under the external force exerted by the external force applying device.

3. The method of claim 2, wherein the base does not equal the linear guide in rigidity.

4. The method of claim 1, wherein the external force applying device is operated with a robotic arm or by hand.

5. The method of claim 1, wherein the external force applying device is one of an impact hammer and a vibration shaker.

6. The method of claim 1, wherein the sensor is a piezoelectric accelerometer, and the sensor is directly attached to the linear guide such that the physical quantity signal received by the sensor relates to acceleration and is sent from the linear guide because of vibration thereof which occurs under the external force.

7. The method of claim 1, wherein the sensor is a microphone, and the sensor is separated from the linear guide by a distance for a sensing purpose such that the physical quantity signal received by the sensor relates to sound pressure and is sent from the linear guide because of vibration thereof which occurs under the external force.

* * * * *